US010440959B2

United States Patent
Barrera Cubillos et al.

(10) Patent No.: US 10,440,959 B2
(45) Date of Patent: Oct. 15, 2019

(54) VIRUS-BASED BIOPESTICIDE

(71) Applicant: Corporación Colombiana de Investigación Agropecuaria—CORPOICA

(72) Inventors: Gloria Patricia Barrera Cubillos, Bogotá (CO); Laura Fernanda Villamizar Rivero, Bogotá (CO); Paola Emilia Cuartas Otalora, Villavicencio (CO); Juliana Andrea Gomez Valderrama, Bogotá (CO)

(73) Assignee: LA CORPORACIÓN COLOMBIANA DE INVESTIGACIÓN AGROPECUARIA—AGROSAVIA, Bogotá D.C. (CO)

( * ) Notice: Subject to any disclaimer, the term of this patent is extended or adjusted under 35 U.S.C. 154(b) by 0 days.

(21) Appl. No.: 15/387,565

(22) Filed: Dec. 21, 2016

(65) Prior Publication Data

US 2017/0172154 A1    Jun. 22, 2017

Related U.S. Application Data

(60) Provisional application No. 62/270,558, filed on Dec. 21, 2015.

(51) Int. Cl.
*A01N 63/02* (2006.01)
*A01N 63/00* (2006.01)
(Continued)

(52) U.S. Cl.
CPC ............ *A01N 63/00* (2013.01); *A01N 25/00* (2013.01); *A01N 63/02* (2013.01); *C12N 7/00* (2013.01);
(Continued)

(58) Field of Classification Search
None
See application file for complete search history.

(56) References Cited

U.S. PATENT DOCUMENTS

| | | |
|---|---|---|
| 5,858,353 A | 1/1999 | Miller et al. |
| 6,096,304 A | 8/2000 | McCutchen |

FOREIGN PATENT DOCUMENTS

| | | |
|---|---|---|
| BR | 0901235-4 | 12/2010 |
| ES | 2301352 A1 | 6/2008 |

(Continued)

OTHER PUBLICATIONS

Villamizar et al. Eudragit S100 microparticles containing Spodoptera frugiperda nucleopolyehedrovirus: Physicochemical characterization, photostability and in vitro virus release. Journal of Microencapsulation, 2010; 27(4): 314-324 (Year: 2010).*

(Continued)

*Primary Examiner* — Michelle S Horning
(74) *Attorney, Agent, or Firm* — The Morales Law Firm; Joseph L. Morales

(57) ABSTRACT

The invention relates to synthetic combinations of two or more pure genotypes cloned from the Colombian wild-type *Spodoptera frugiperda* nucleopolyhedrovirus isolate (NPV003=SfCOL) and to biopesticidal compositions having an active ingredient comprising at least two synthetic combinations and, optionally, a *S. frugiperda* granulovirus. The compositions of the invention may contain ultraviolet protectants, diluents, coating polymers, surfactants and/or pH regulators and are effective for the biological control of insects in crops, such as corn, rice, cotton, sugarcane and grasses.

9 Claims, 7 Drawing Sheets

Specification includes a Sequence Listing.

(51) Int. Cl.
A01N 25/00 (2006.01)
C12N 7/00 (2006.01)
(52) U.S. Cl.
CPC .............. C12N 2710/14121 (2013.01); C12N 2710/14131 (2013.01)

(56) References Cited

FOREIGN PATENT DOCUMENTS

| WO | 2011117411 A1 | 9/2011 |
| WO | 2014161974 A1 | 10/2014 |
| WO | 2014182228 A1 | 11/2014 |

OTHER PUBLICATIONS

Kurmen et al. Microencapsulation of a Colombian Spodoptera frugiperda Nucleopolyhedrovirus with Eudragit® S100 by Spray Drying. Braz. Arch. Biol. Technol. v.58 n. 3: pp. 468-476, May/Jun 2015 (Year: 2015).*
Cuartas et al. The Complete Sequence of the First Spodoptera frugiperda Betabaculovirus Genome: A Natural Multiple Recombinant Virus. Viruses 2015, 7, 394-421. (Year: 2015).*
Gomez et al. Microencapsulated Spodoptera frugiperda nucleopolyhedrovirus: insecticidal activity and effect on arthropod populations in maize. Biocontrol Science and Technology. vol. 23, Issue 7, p. 829-846. (Year: 2013).*
Cuartas et al. Characterisation of a Colombian granulovirus isolated from Spdoptera frugiperda larvae. Biocontrol Science and Technology. 2014. vol. 24, No. 11, p. 1265-1285. (Year: 2014).*
Barrera et al., Deletion Genotypes Reduce Occlusion Body Potency but Increase Occlusion Body Production in a Colombian Spodoptera frugiperda Nucleopolyhedrovirus Population. (2013) PLOS ONE, vol. 8, Issue 10.
Villamizar et al., Eudragit S100® microparticles containing Spodoptera frugiperda nucleopolyhedrovirus: Physicochemical characterization, photostability and in vitro virus release, (2010),Journal of Microencapsulation 27: 314-24.

Camacho et al., Microencapsulation of a Colombian Spodoptera frugiperda Nucleopolyhedrovirus with Eudragit S100® by spray drying, (May 2015) Brazilian Archives of Biology and Technology. vol. 58, n.3: pp. 468-476.

Simon et al., Genetic structure of a Spodoptera frugiperda nucleopolyhedrovirus population: High prevalence of deletion genotypes, (2004), Applied and Environmental Microbiology 70: 5579-5588.

Simon et al., Functional importance of deletion mutant genotypes in an insect nucleopolyhedrovirus population, (2005) Applied and Environmental Microbiology 71, 4254-4262.

Gomez et al., Microencapsulated Spodoptera frugiperda nucleopolyhedrovirus: insecticidal activity and effect on arhropod populations in maize. (2013) Biocontrol Science and Technology, 23(7): 829-846.

Santos, Nucleopoliedrovirus de Spodoptera frugiperda SfNPV003: compatibilidad con agroquimicos y estabilidad en condiciones de almacenamiento. (2014) Corpoica Cienc. Tecnol. Agropec., 15(2): 219-228.

Moscardi, Use of viruses for pes control in Brazil: the case of nuclear polyhedrosis virus of the soybean caterpilar, *Anticarsia gemmatalis*, (1989) Mem. Inst. Oswaldo Cruz, Rio de Janeiro, 84(3): 51-56.

Boucias, D.G., Pendland, J.C. 1998. Baculoviruses, in: Kluwer (Ed.), Principles of insect pathology. Academic Publishers, Norwell, pp. 111-146.

Braunagel and Summers, Autographa califomica nuclear polyhedrosis virus, PDV, and ECV viral envelopes and nucleocapsids: structural proteins, antigens, lipid and fatty acid profiles, (1994) Virology 202: 315-328.

Duffy et al., Sequence analysis and organization of the Neodiprion abietis nucleopolyhedrovirus genome, (2006) Journal of Virology 80: 6952-63.

Behle, R. W. et al. Laboratory and field evaluations of the efficacy of a fast-killing baculovirus isolated from Spodoptera frugiperda. Journal of invertebrate pathology, Feb. 2012,109(2): 194-200.

Gomez et al., Aislamiento, identificación y caracterización de nucleopoliedrovirus nativos de Spodoptera frugiperda en Colombia. [Isolation, identification and characterization of Spodoptera frugiperda wild-type nucleopolyhedrovirus in Colombia, (2010), Revista Facultad Agronomia. Medellin 63: 5511-5520.

Malagón, A.L. (2014)Estabilidad de dos variantes genotipicas del nucleopoleidovirus de Spodoptera frugiperda a través de ciclos sucesivos de infección en larva. Tesis Magister en ciencuas Microbiologia, Universidad Nacional de Colombia.

Herniou et al., The genome sequence and evolution of baculoviruses, (2003), Annual Review of Entomology 48: 211-34.

Herniou et al., Ancient coevolution of baculoviruses and their insect hosts. (2004) Journal of Virology 78: 3244-51.

Hughes and Wood, A synchronous peroral technique for the bioassay of insect viruses.(1981) Journal of Invertebrate Pathology 37: 154-159.

Barrera et al., Spodoptera frugiperda multiple Nucleopolyhedrovirus as a potential biological insecticide: Genetic and phenotypic comparison of field isolates from Colombia Biological control, Aug. 2011, 58(2):113-120.

Inceoglu et al., Genetically modified baculoviruses: a historical overview and future outlook. (2006) Advances in virus research 68: 323-360.

Jehle et al., Molecular identification and phylogenetic analysis of baculoviruses from Lepidoptera. (2006) Virology 346: 180-193.

Jenkins, N. & Grzywacz, D. 2003. Towards the standardization of quality control of fungal and viral biocontrol agents. In Qual Control Prod Biol Control agents theory Test Proced, pp. 247-263. Edited by J. C. van Lenteren. Wallinford, UK: CAB International.

Lahlalia et al., Studying and modelling the combined effect of temperature and water activity on the growth rate of P. Expansum, (2006), International Journal of Food Microbiology. 103:315-322.

Lasa et al., Efficacy of Spodoptera exigua multiple nucleopolyhedrovirus as a biological insecticide for beet armyworm control in greenhouses of southern Spain, (2007), Biocontrol Science and Technology 17: 221-232.

Miele et al., Baculovirus: molecular insights on their diversity and conservation. (2011), Int. Journal of Evolutionary Biology 211: 37-42.

Muñoz et al., Naturally occurring deletion mutants are parasitic genotypes in a wild-type nucleopolyhedrovirus population of Spodoptera exigua, (1998) Applied and Environmental Microbiology 64: 4372-4377.

Muñoz et al., Four genotypic variants of a Spodoptera exigua nucleopolyhedrovirus (Se-SP2) are distinguishable by a hypervariable genomic region, (1999), Virus Research 59: 61-74.

Murillo et al., Genetic and phenotypic variability in Spodoptera exigua nucleopolyhedrovirus isolates from greenhouse soils in southern Spain. (2006) Biological Control 38: 157-175.

Wang and Jehle, Nudiviruses and other large, stranded circular DNA viruses of invertebrates: New insights on an old topic, (2009) Journal of Invertebrate Pathology 101: 187-193. Zar, J. 1999.

Santos et al., Effect of the formulation on the shelf life of biopesticides based on two Colombian isolates from Trichoderma koningiopsis Th003 and Trichoderma asperellum Th034, (2012) Revista Iberoamericana de Micologia 29:150-156.

Villamizar et al., Implementation of quality control techniques for the production of a biopesticide based on Phthorimaea operculella granulovirus Phop GV, (2005) Revista Colombiana de Entomologia 31: 127-32.

Shapiro, Congo red as an ultraviolet protectant for the gypsy moth (*Lepidoptera*:Lymantriidae) nuclear polyhedrosis virus.(1989) Journal of Economical Entomology. 82: 548-550.

Slack and Arif, The baculoviruses occlusion-derived virus: Virion structure and function, (2007), Advances in virus research 69: 99-165.

(56) References Cited

OTHER PUBLICATIONS

Theilmann et al., Family baculoviridae. In: Fauquet, C.M., Mayo, M.A., Maniloff, J., Desselberger, U., Ball, L.A. (Eds.), (2005) Virus Taxonomy, Eighth Report of the International Committee on Virus Taxonomy. Elsevier Press, San Diego, pp. 177-185.

* cited by examiner

VIRUS-BASED BIOPESTICIDE

CROSS-REFERENCE TO RELATED APPLICATIONS

This application is a non-provisional application claiming priority under 35 U.S.C. § 119(e)(1) from provisional application Ser. No. 62/270,558, filed on Dec. 21, 2015, and which is herein incorporated by reference in its entirety.

BACKGROUND OF THE INVENTION

Field of Invention

The invention pertains to the agricultural sector, specifically to biopesticides for biological control of pests.

Background of the Invention

Baculoviruses (from Latin baculum=staff) are viruses that specifically infect insects, mainly members of orders Lepidoptera, Hymenoptera and Diptera (Wang & Jehle, 2009; Duffy et al., 2006; Herniou et al., 2003; Boucias et al., 1998). They are found in the environment as occlusion bodies (OBs) (Slack & Arif, 2007), which are protein structures that protect the virions and grant them increased endurance in the environment.

The Baculoviridae family is characterized by the fact that its members contain a circular, double-stranded DNA genome, ranging from 80 to 180 kilobase pairs (kbp). The family comprises four genera, classified according to their structural, molecular and biological characteristics: alphabaculovirus consists of nucleopolyhedroviruses (NPVs) isolated from lepidopterans, betabaculovirus consists of granuloviruses (GVs) isolated from lepidopterans, deltabaculovirus consists of NPVs isolated from dipterans, and gammabaculovirus consists of NPVs isolated from hymenopterans (ICTV, 2012; Jehle et al., 2006; Miele et al., 2011).

These genera are distinguished by their structural characteristics, such as the morphology of their occlusion bodies as well as by some biological aspects (Herniou et al., 2004; Jehle et al., 2006). Throughout the infection cycle, the formation of two viral phenotypes has been observed: budded virions (BVs) and occlusion-derived virions (ODVs) (Theilmann et al., 2005). The two phenotypes have similar nucleocapsid structures and contain identical genetic information, but the source and composition of their envelopes is different (Funk et al., 1997; Braunagel & Summers, 1994). BVs are responsible for effecting the systemic infection of the host, while ODVs are responsible for spreading the virus between hosts. Baculoviruses are found in the environment as occlusion bodies (OBs); said bodies keep them viable for prolonged periods of time. While the OBs of GVs normally contain only one (1) virion, the OBs of NPVs may contain multiple virions, and furthermore, said virions may in turn contain multiple nucleocapsids. (FIG. 1). There are various studies concerning the use of Baculoviruses as regulation factors of some populations of insects, especially those that affect agricultural production. This technology offers considerable advantages over chemical pesticides, including the reduction of toxic residues in food products and soil, as well as lower health hazards.

WO2014/182228 describes a method for increasing the insecticidal efficacy of a pathogenic microorganism (*Spodoptera frugiperda* nucleopolyhedrovirus (SfNPV)) by means of its association with a mutualistic organism (yeast species of the Metschnikowia genus, such as *Ascomycota* and *Sacharomycetes*; yeast species of *Candida*; species of *Cryptococcus* and species of *Pseudozyma*) that co-exists in intimate association with the larva and that stimulates the ingestion of the pathogen by said larva. However, the drawback of said method is that during the storage period, the metabolic activity of the mutualistic organism can continue, thereby producing metabolites that alter viral activity, and thus, the quality of the product.

WO2011/117411 titled "*Entomopathogenic Viral Preparation*", discloses a composition containing at least one *Cydia pomonella* granulovirus (characterized by a specific restriction fragment pattern), used to control the codling moth larva *Cydia pomonella* (Lepidoptera:Tortricidae) and the Oriental peach moth *C. molesta*. The composition disclosed therein does not have any application for the control of migratory pests from tropical and subtropical zones of America, such as the fall armyworm *S. frugiperda*.

In addition to the formulations and combinations of aforementioned agents, some studies have focused on the genetic diversity of the control agents against specific pests, with the goal of selecting highly pathogenic isolates. Patent WO2014/161974 relates to new genotypes of *Chrysodeixis chalcites* nucleopolyhedrovirus (Chch SNPV), the process for production thereof and uses thereof as biological control agents. Patent application ES2301352 discloses six new genotypes of *S. exigua* multiple nucleopolyhedrovirus termed AlPstM0935, AlPstM1400, AlPstM1033, AlPstM1449, AlPstM0923, and AlPstM0657, and uses thereof, preferably as a combination of two or more genotypes, in insecticidal compositions against *S. exigua*.

In the last few decades, various strategies to genetically modify Baculovirus have been employed in order to increase its virulence, pathogenicity and/or insecticidal activity, which include the following:

a) insertion of the gene coding for the toxin produced by the scorpion *Buthus eupus*;

b) insertions of the gene coding for the esterase of the juvenile hormone produced by *Heliothis virescens*;

c) insertion of the gene for TxP-1 toxin;

d) insertion of the gene for AaIT toxin from the scorpion *Androctonus australis* into AcNPV (*Autographa californica* nucleopolyhedrovirus);

e) insertion of the gene for the cry toxin produced by *Bacillus thuringiensis*;

f) insertion of the gene for diuretic hormone; g) insertion of the scorpion neuroselective neurotoxin LqhIT2;

g) insertion of sequences that express substances that suppress the appetite of *Helicoverpa zea* and related pests (see Brazilian patent PI0901235-4 and patent U.S. Pat. No. 6,096,304); and h) modification of the gene for chitinase, to attenuate the lysis of the larva and increase the yield and recovery of virions for mass production.

Although the genetic modification strategies have been shown to improve the characteristics of the modified baculoviruses, the environmental policies of several European and Latin American countries, including Colombia, do not allow the use of genetically modified organisms, because of which these microorganisms cannot be easily applied on an industrial scale or in crop fields.

For that reason, it has been necessary to develop various types of biopesticidal formulations based on unmodified organisms that are highly specific against the pests faced and that overcome the drawbacks associated with low efficacy and high sensitivity to UV radiation. Thus, in the study titled "*Deletion Genotypes Reduce Occlusion Body Potency but Increase Occlusion Body Production in a Colombian Spodoptera frugiperda Nucleopolyhedrovirus Population*", Corpoica describes the purification of genotypes from a native isolate of *S. frugiperda* multiple nucleopolyhedrovirus (SfMNPV). This study reports the production of 83 clones, 10 of which corresponded to different genotypes and were subjected to molecular and biological characterization. The results showed that one genotype was more pathogenic.

The study also demonstrated that the combination of this more pathogenic genotype (termed A) with three other selected genotypes (termed C, D, and E) exhibited a lower or equal potency to that of the wild-type virus. The conclusion of said study was that the co-occluded combination of various genotypes in the wild is a pathogenicity regulation mechanism to ensure the persistence of the pathogen in nature and may result in lower insecticidal activity than the original wild-type virus (Barrera et al., 2013).

Additionally, in another study titled "*Eudragit S100® microparticles containing Spodoptera frugiperda nucleopolyhedrovirus*: Physicochemical characterization, photostability and in vitro virus release", Corpoica reports a method for microencapsulation of occlusion bodies of the NPV001 isolate from *S. frugiperda* nucleopolyhedrovirus, using a Eudragit S100® methacrylic acid polymer, by means of the emulsion and solvent evaporation method. The microcapsules produced exhibited a loss of efficacy after 2 hours of irradiation with ultraviolet light (Villamizar et al., 2010), possibly due to the absence of other formulation aids and to the fact that the active ingredient is a complete wild-type virus.

In a later study titled "*Microencapsulation of a Colombian Spodoptera frugiperda Nucleopolyhedrovirus with Eudragit S100® by spray drying*", Corpoica reports a formulation that is similar to the previous formulation, but with an improved microencapsulation process, abandoning the solvent evaporation method in favor of a fluidized bed granulation method (Camacho et al., 2015). In this study, the size of the microcapsules was decreased to 20 µm and photostability to UV exposure increased.

The interaction of the various genotypes that comprise a nucleopolyhedrovirus isolate may have negative, neutral or positive effects. For example, pure genotypes of *S. exigua* nucleopolyhedrovirus (SeMNPV) exhibited greater insecticidal activity that the complete wild-type virus (Muñoz et al., 1998). However, in a *S. frugiperda* nucleopolyhedrovirus isolate from Nicaragua, the complete wild-type virus exhibited a greater pathogenicity than the pure genotypes (Simón et al., 2004; 2005). Furthermore, the combination of some genotypes restored the pathogenicity of the pure genotypes, but never achieved a greater pathogenicity than that exhibited by the wild-type isolate.

The inventors designed combinations of two or more pure genotypes cloned from the *Spodoptera frugiperda* nucleopolyhedrovirus isolate (NPV015 through NPV019) that exhibited a greater pathogenicity than the wild-type genotype.

SUMMARY OF THE INVENTION

The present invention relates to biopesticidal compositions comprising synthetic combinations of two or more highly pathogenic genotypes of *S. frugiperda* NPV having a greater insecticidal activity than that of the wild-type virus, and optionally, biological enhancers to increase their pathogenicity. The compositions exhibit a high efficacy against *Spodoptera frugiperda* (fall armyworm), are photoresistant and stable at ambient temperature.

The invention also provides a novel formulation for coating the active ingredient, comprising various formulation aids (e.g. UV filters) in order to facilitate its implementation, protect it from light and prolong its shelf life without the need for refrigeration.

ODVS: several ODVs, V: virion, NC: nucleocapsid.

Figure 1:
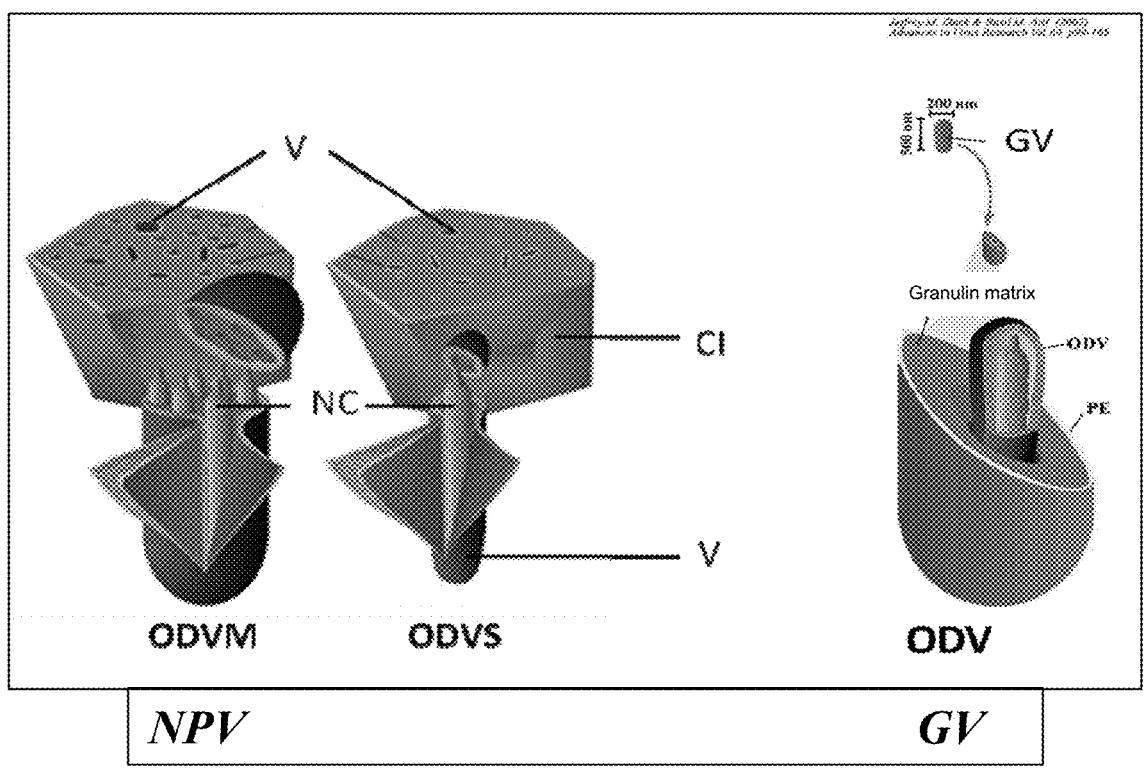
FIG. 1: Diagram of the structure of baculoviruses. It represents the structure of the two morphologies of baculoviruses: Nucleopolyhedrovirus (ODVM and ODVS) and granulovirus (GV). ODVM (multiple virions) and ODV (single virion or single nucleopolyhedrovirus SNPV) are immersed in an occlusion body (CI or OB) consisting of a protein matrix termed polyhedrin in NPVs and granulin in GVs.
Figure 2:
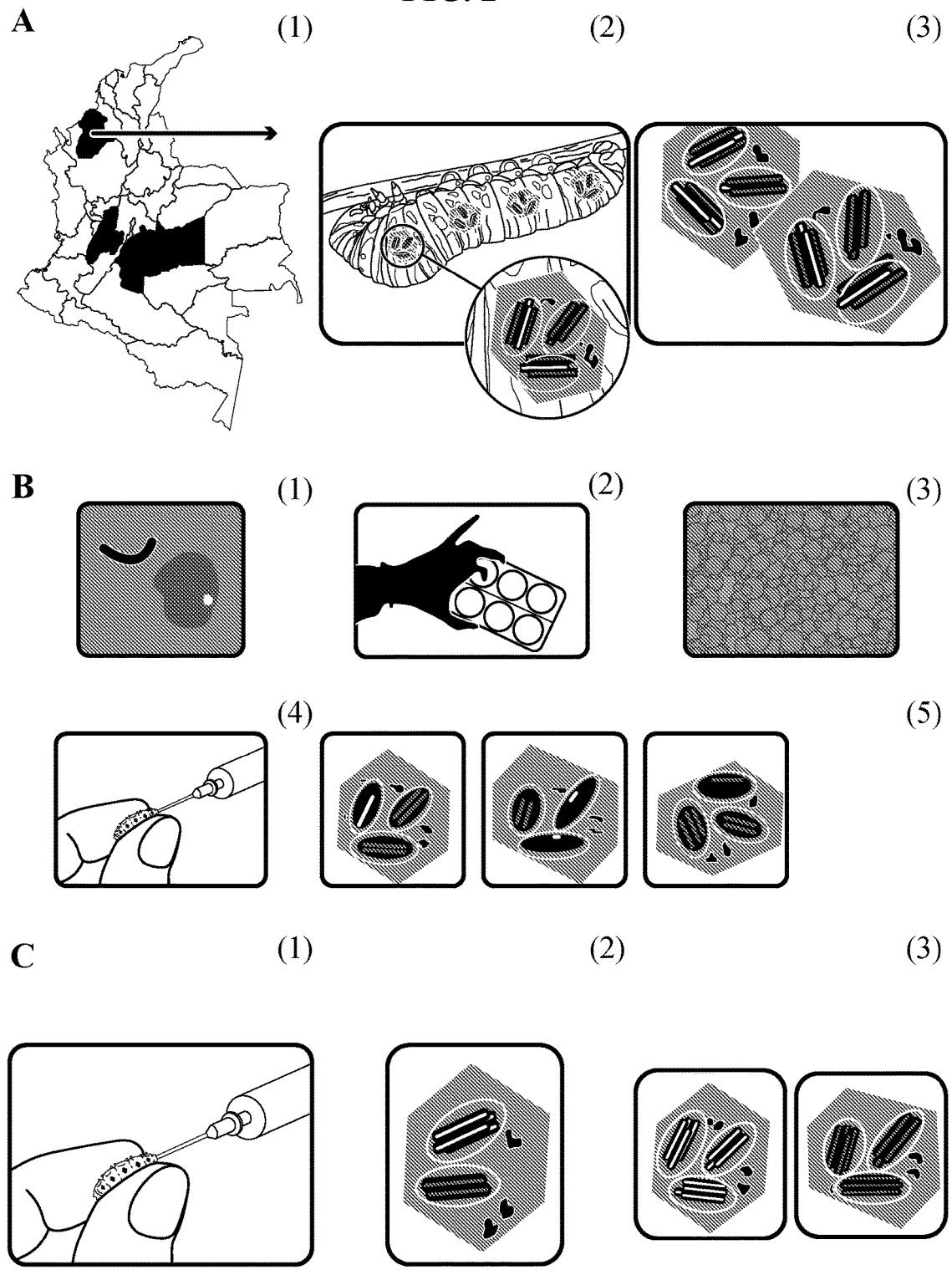

FIG. 2: Diagram of the process for obtaining genotypes of *Spodoptera frugiperda* nucleopolyhedrovirus.
A. Obtaining a wild-type SfMNPV isolate
B. Obtaining individual genotypic variants
C. Preparation of synthetic combinations of the virus.

Figure 3:
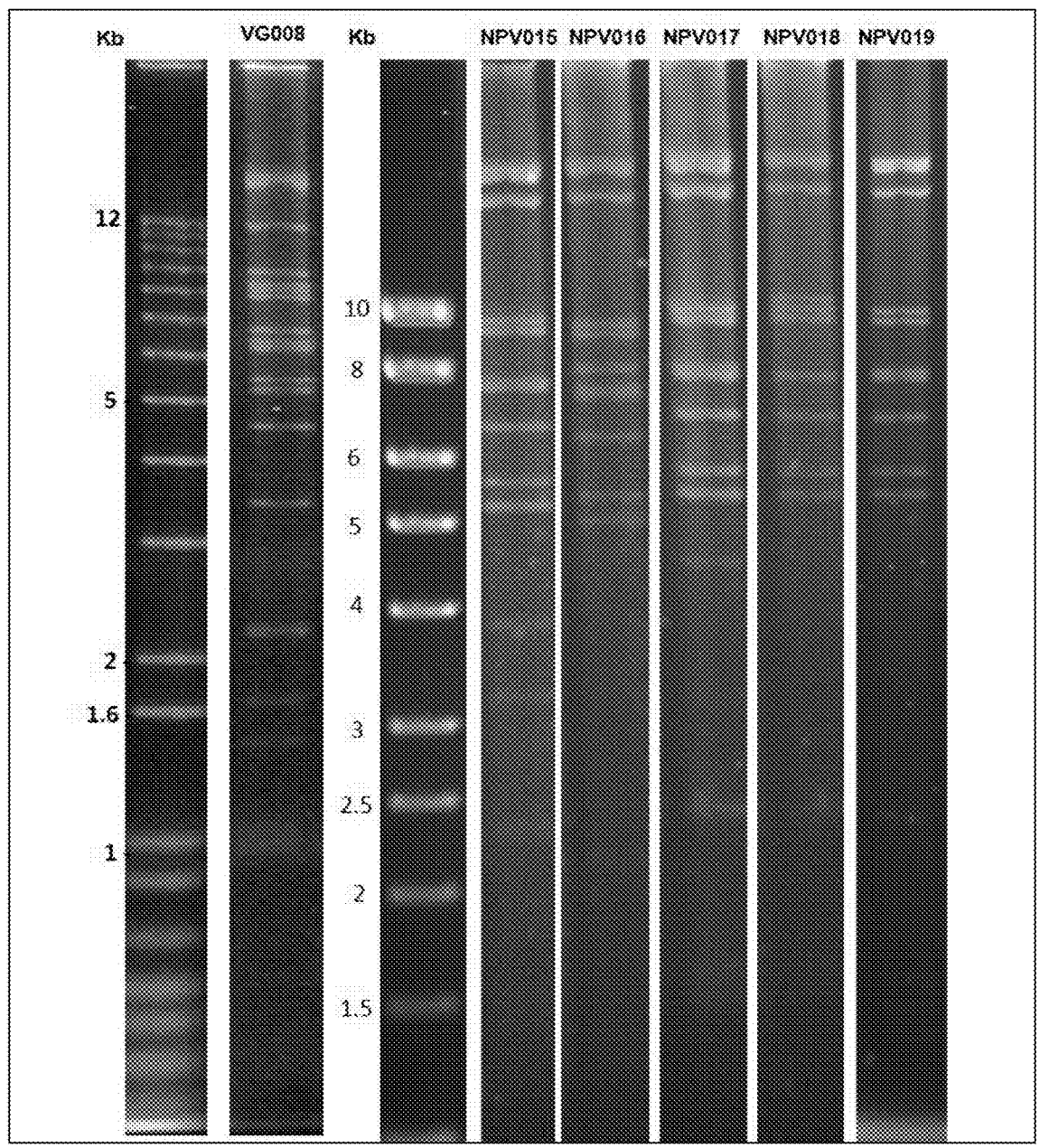

FIG. 3: Photograph of the agarose gel with restriction fragment patterns (REN) produced by the PstI enzyme from the *Spodoptera frugiperda* granulovirus isolate VG008 and the genotypes of *S. frugiperda* nucleopolyhedrovirus NPV015-NPV019.

Figure 4:
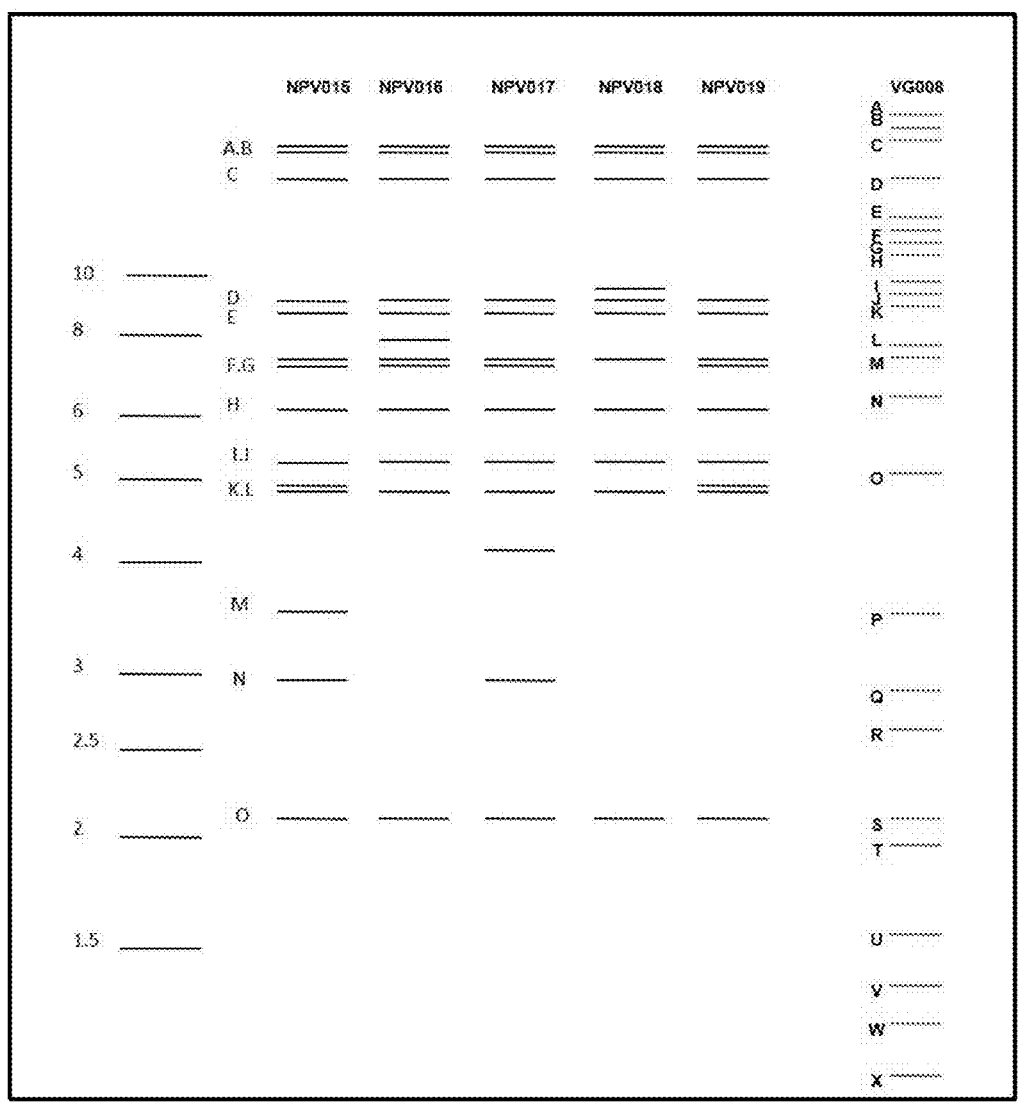

FIG. 4: Diagram of the fragments produced by the PstI enzyme from the *Spodoptera frugiperda* granulovirus isolate VG008 and the genotypes of *S. frugiperda* nucleopolyhedrovirus NPV015-NPV019.

Figure 5:
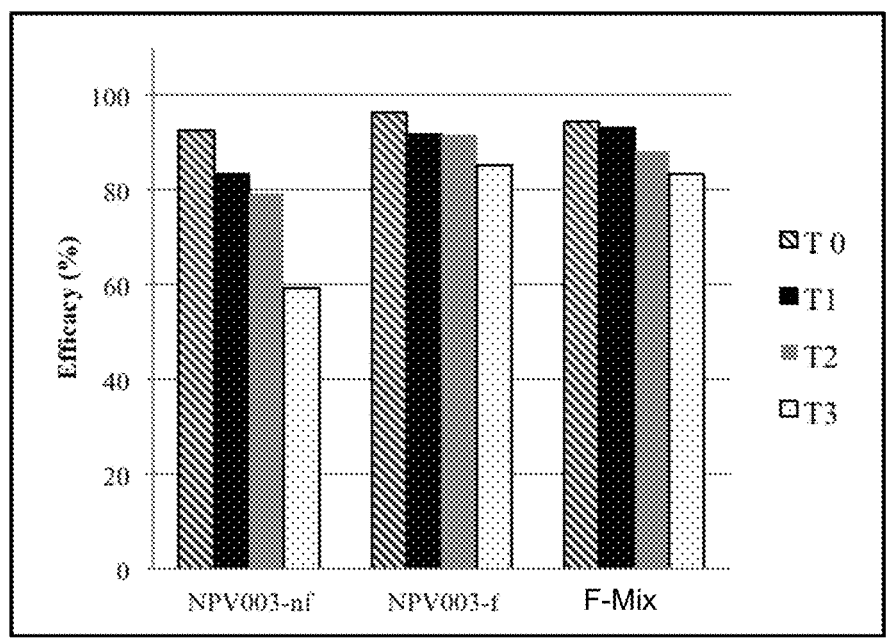

FIG. 5: Graph of the effect of the formulation on the stability of the insecticidal activity of the wild-type virus NPV003 and the combination of genptNPV0es and granulovirus at 28° C.
NPV003-nf: Unformulated wild-type virus NPV003; NPV003-f: Formulated wild-type virus NPV003 and formulated granulovirus.

Figure 6:
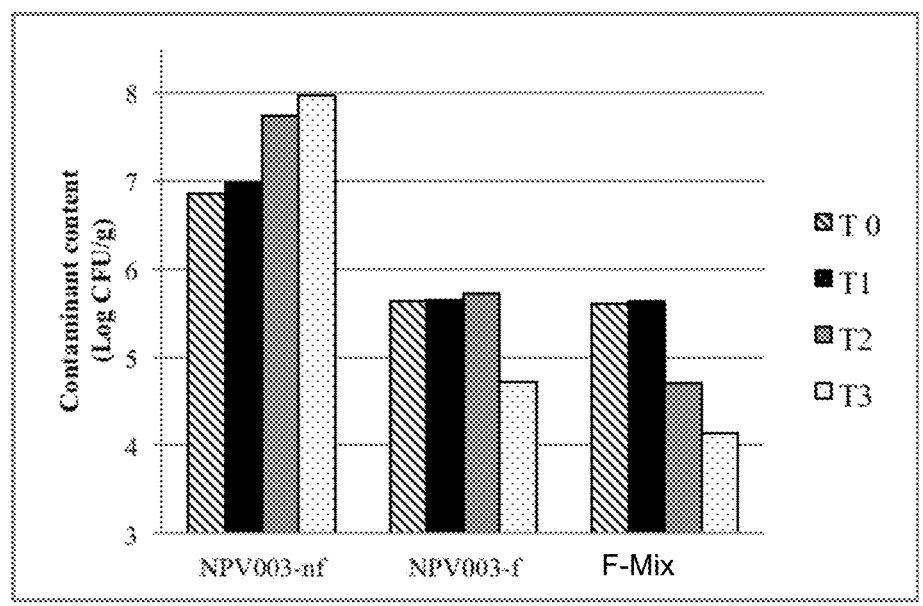

FIG. 6: Graph of the contaminating microorganism content of the formulated and unformulated wild-type virus NPV003 and of the formulated combination of genotypes and granulovirus, stored for three months at 28° C.
NPV003-nf: Unformulated wild-type virus NPV003; NPV003-f: Formulated wild-type virus NPV003 and formulated granulovirus.

Figure 7:
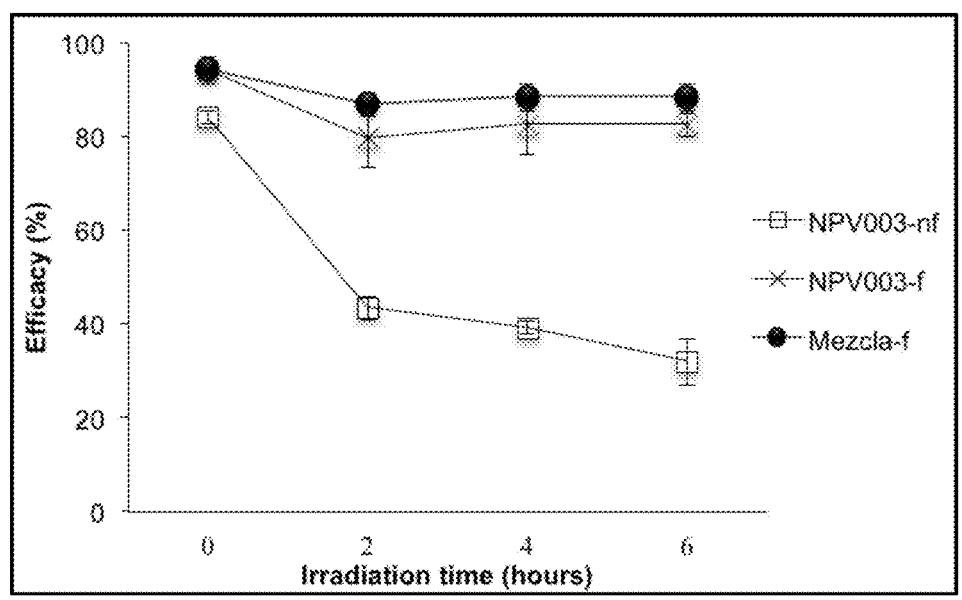

FIG. 7: Graph of efficacy vs irradiation time from the photostability study of the formulated and unformulated wild-type virus NPV003 and of the formulated combination of genotypes and granulovirus
NPV003-nf: Unformulated wild-type virus NPV003; NPV003-f: Formulated wild-type virus NPV003 and formulated granulovirus.

DETAILED DESCRIPTION OF THE INVENTION

The present invention comprises a synthetic combination of two or more pure genotypes cloned from the isolate of nucleopolyhedrovirus (NPV015 through NPV019) from *Spodoptera frugiperda* (NPV-003=SfCOL), co-occluded in a single occlusion body, or a combination of occlusion bodies of individual genotypes, and optionally, a biological or chemical enhancer (e.g. granulovirus isolates, insect nucleopolyhedroviruses or proteins derived therefrom). The invention also considers compositions comprising said synthetic combinations along with one or more excipients, adjuvants and/or carriers that are chemically and environmentally suitable for this type of product.

The pure genotypes can be obtained in accordance with the process described in FIG. 2. A purified viral suspension of NPV0003 is used to infect Spodoptera frugiperda larvae by oral administration, and hemolymph is extracted from the larvae at the specific point in the cycle during which budded virions are present (with a single nucleocapsid and a single genome). Then, by means of several dilutions, insect cells of the Sf9 line (S. frugiperda cell line) are infected.

In order to obtain the combinations of co-occluded genotypes in a single occlusion body, the occlusion-derived virions can be released by means of treatment with alkaline solutions, so they can later be injected simultaneously into the larvae. The co-occlusion of the selected genotypes occurs during the infection process.

In order to obtain the combination of occlusion bodies having individual genotypes, individual cells containing a single genotype are selected and multiplied by means of injection into larvae, from which each individual genotype variant is purified after the death of the larvae. From these individual genotypes, combinations of the genotypes that were previously selected for their insecticidal activity can be produced.

In one embodiment of the invention, all of the genotypes of nucleopolyhedrovirus NPV003 and the *S. frugiperda* granulovirus isolate VG008 can be digested with PstI enzyme and the resulting bands can be observed in 1% agarose gel stained with ethidium bromide (FIG. 3). The restriction fragments resulting from the digestion of genomic DNA by PstI enzyme are labeled alphabetically, beginning with the letter A for the largest fragment and consecutively down to the smallest resulting fragment (FIG. 4).

The genotypes of nucleopolyhedrovirus and granulovirus are characterized by a specific band pattern resulting from genome cleavage with PstI enzyme, with fragments of different weights. Table 1 shows the estimated size of the restriction fragments produced by the PstI enzyme from the *S. frugiperda* granulovirus isolate VG008 and the genotypes of *S. frugiperda* nucleopolyhedrovirus NPV015 through NPV019.

TABLE 1

| Fragment | NPV015 | NPV016 | NPV017 | NPV018 | NPV019 | VG008 |
|---|---|---|---|---|---|---|
| A | 28084 | 28084 | 28084 | 28084 | 28084 | 14750 |
| B | 24926 | 24926 | 24926 | 24926 | 24926 | 14749 |
| C | 12465 | 12465 | 12465 | 12465 | 12465 | 14749 |
| C' | | | | 9200 | | |
| D | 8864 | 8864 | 8864 | 8864 | 8864 | 11761 |
| E | 8481 | 8481 | 8481 | 8481 | 8481 | 8921 |
| E' | | 7800 | | | | |
| F | 7079 | 7079 | 7079 | | 7079 | 8784 |
| G | 6932 | 6932 | 6932 | 6932 | 6932 | 8397 |
| H | 6124 | 6124 | 6124 | 6124 | 6124 | 8030 |
| I | 5182 | 5182 | 5182 | 5182 | 5182 | 6969 |
| J | 4899 | 4899 | 4899 | 4899 | 4899 | 6660 |
| K | 4887 | | | 4887 | 4887 | 6430 |
| L | 4769 | 4769 | 4769 | 4769 | 4769 | 5474 |
| L' | | | 4200 | | | |
| M | 3575 | | | | | 5258 |
| N | 2953 | | | | | 4552 |
| N' | | | 2700 | | | |
| O | 2112 | 2112 | 2112 | 2112 | 2112 | 3485 |
| P | 1339 | 1339 | 1339 | 1339 | 1339 | 2212 |
| Q | 1228 | 1228 | 1228 | 1228 | 1228 | 1705 |
| R | | | | | | 1447 |
| S | | | | | | 1039 |
| T | | | | | | 974 |
| U | | | | | | 636 |
| V | | | | | | 521 |
| W | | | | | | 400 |
| X | | | | | | 300 |
| Total | 133899 | 130284 | 129384 | 129492 | 127371 | 138203 |

The bands that characterize each genotype are:

NPV015: A, B, C, D, E, F, G, H, I, J, K, L, M, N, O, P, Q

NPV016: A, B, C, D, E, E', F, G, H, I, J, L, O, P, Q

NPV017: A, B, C, D, E, F, G, H, I, J, L, L', N', O, P, Q

NPV018: A, B, C, C', D, E, G, H, I, J, K, L, O, P, Q

NPV019: A, B, C, D, E, F, G, H, I, J, K, L, O, P, Q

VG008: A, B, C, D, E, F, G, H, I, J, K, L, M, N, O, P, Q, R, S, T, U, V, W, X

The sequences of the amplified fragments are:

```
>Sf23
                                          (SEQ ID. No. 1)
GCTTGTGCGTTGTCGTTGATCGTACAGAGATAATAACTAAAATACACCCC

ATCACTAAGAAAAAAATTAAAATTGACGTATCTAATAAATACATTAATAG

GATGAAGAAGACGCTGATAAAGTGGGGCTATCCTGTGAAATTTGCAAAAT

TTGACGAGTTTAAAGGATACAAGTACGACATTGACACGGACGACTGGGAC

CGAGTCGACTACAA

>Sf24
                                           (SEQ ID No. 2)
TCGTCGGCATCATACTGCTCTCGGTGGACAAGTTTGTGTCCATACCCATC

ATACAGCTGTACCAGATCGCGTACCAGCAACTGCAGATATCGCCGTTTTA

CGTGACGCTGACGCTCATGCTGCTCACCACCGTTGGTGGACTGTCGACGA

AAACCATGCGAACGTG
```

The isolate VG008, for its part, amplified a specific 203 bp region with the primers SFGV 24.1-5' CCGATAAGGT-TATATCTGA 3' (SEQ ID No. 3) and SFGV 24.2 5'

TCAATAACTTCTTCGTGCA 3'. (SEQ ID No. 4) The sequence of the amplified fragment is the following:

>SFGV24
(SEQ ID No. 5)
AGATATCACCTTTGAAGACATTGATTCGATCTACGACGCAGAAACGCAAC

TCGACAAAGCTTACGATAACGTTAAATGGGAGGACAAATACAAGGAATTG

CTAGACCAATACAATAAAGATAAAGAAAAATGGGAGAAAAAATACACAGA

GCTTATGAATCAAAATACAGTCGACGAGGACAAATGGACAACAGAAAAGA

AGA

The genotypes of the nucleopolyhedrovirus (NPV015, NPV016, NPV017, NPV018, NPV019) are also characterized by the amplification of two specific 214 and 166 base-pair fragments with the primers Sf23.1 (5'-GCTTGT-GCGTTGTCGTTGAT-3') (SEQ ID No. 6) and Sf23.2 (5'-TTGTAGTCGACTCGGTCCCA-3') (SEQ ID No. 7), and with the primers Sf24.1 (5'-TCGTCGGCATCATACT-GCTC-3') (SEQ ID No. 8.) and Sf24.2 (5'-CACGTTCG-CATGGTTTTCGT-3') (SEQ ID No. 9) respectively. This region, that is present and specific to all of these genotypes, was not found in other wild-type isolates. The genotypes of the nucleopolyhedrovirus (NPV015, NPV016, NPV017, NPV018, NPV019) are deposited in the Nation's germplasm bank for microorganisms pertaining to biological control, managed by Corpoica and located at the Centro de Investigaciones Tibaitatá [Tibaitatá Research Center], Mosquera (Cundinamarca, Colombia). The biological materials have also been deposited with the American Type Culture Collection under accession number SD-7011.

In one embodiment of the invention, the synthetic combination comprises at least the genome of a virions that exhibits the band pattern resulting from cleavage with PstI enzyme, listed in Table 1.

In a more preferred embodiment, the synthetic genotype combinations are:
1. Synthetic combination No. 1: NPV015+NPV016+NPV017;
2. Synthetic combination No. 2: NPV015+NPV018+NPV019;
3. Synthetic combination No. 3: NPV015+NPV016+NPV017+VG008;
4. Synthetic combination No. 4: NPV015+NPV018+NPV019+VG008;
5. Synthetic combination No. 5: NPV015+NPV018+NPV017+VG008 protein;
6. Synthetic combination No. 6: NPV015+NPV018+NPV019+VG008 protein.

Synthetic combinations 1 through 4 are obtained in accordance with the process illustrated in FIG. 2. For the specific case of synthetic combinations 5 and 6, once the combinations of viral genotypes are obtained, VG008 proteins are added as enhancers. The VG008 proteins can correspond to the total or partial protein extract obtained from the occlusion bodies, to the proteins purified therefrom, or synthetically produced proteins. The main proteins are of the enhancin and chitinase varieties.

The synthetic combinations can be included in biopesticidal compositions. In addition to the synthetic NPV combinations, the compositions also include various carriers, coadjuvants, ultraviolet protectants, diluents, coating polymers, surfactants and pH regulators in order to establish the proprietary shape and characteristics of the end product (e.g. form emulsions), improve its stability and increase its shelf life during storage. The total concentration of synthetic combinations in the compositions of the invention is preferably between 0.1% and 99.9% (w/w).

For the purposes of the present invention, a carrier can be defined as a substance or mixture of substances (e.g. solvents, solutions, emulsions and suspensions) capable of holding the synthetic combinations without affecting their ability to perform their desired function.

The ultraviolet protectants are selected from the group consisting of: pigments, such as iron oxides, titanium dioxide, zinc dioxide; coloring agents, such as lycopene, betaine, bixin, curcumin, chlorophyll, tartrazine, saffron, carminic acid, other food coloring agents and optical brighteners, such as stilbene derivatives.

The diluents are selected from the group consisting of: clays, such as kaolin, bentonites, sepiolites, starches, cellulose derivatives and stearates, such as magnesium stearate. The coating polymers are selected from the group consisting of: natural polymers, such as lignin, cellulose, starch, carrageenan, alginate, gum arabic, xanthan gum, dextrans, synthetic polymers, such as acrylic derivatives (polymethyl acrylates) and polyesters.

The pH regulators are selected from the group consisting of: buffers, such as phosphate, citrate, carbonate, borate phthalate buffer and combinations thereof. The surfactants are selected from the group consisting of: anionic surfactants, such as carboxylate esters and polyethoxylated carboxylate derivatives; cationic surfactants, such as benzalkonium chloride and cetylpyridinium chloride; nonionic surfactants, such as polysorbates (TWEEN 20-80), sorbitan esters (SPAN 20-80) and octyl phenol ethoxylate (TRITON); and amphoteric surfactants, such as betaines and sultaines.

The compositions of the invention can be in solid form as powders, granules, tablets or pellets, in liquid form as suspensions, emulsifiable concentrates or emulsions, and can be applied to foliage, to soil, by dusting, by irrigation and/or by spraying, and can be mixed with compost, fertilizers, other bio-additives, vegetable extracts and agrochemicals. Additionally, the compositions can optionally contain biological or chemical enhancers of insecticidal activity.

The concentration of occlusion bodies in the active ingredient of the compositions is between $1 \times 10^4$ and $1 \times 10^{11}$ occlusion bodies/mL in all of the synthetic viral combinations described hereinbefore. The compositions include different coadjuvants with specific functions to improve stability during storage and the photostability of the viral particles under solar radiation.

In an additional preferred embodiment, the compositions of the invention are formulated as a wettable powder, which includes a bioadhesive polymer that mitigates the effect of solar radiation and increases the adhesion of the virus to plant tissue and the intestinal mucosa of the insect. The specific compositions of this composition stabilize the occlusion bodies of the virus during storage, thereby increasing the shelf life of the bioproduct.

Some of the preferred embodiments of the compositions of the present invention are described in Tables 2 through 7.

TABLE 2

Wettable powder composition - base

| COMPONENT | (% w/w) on a dry basis |
|---|---|
| Viral suspension with a concentration between $10^4$ and $10^{11}$ occlusion bodies/mL* | 0.50-8.50 |

TABLE 2-continued

Wettable powder composition - base

| COMPONENT | (% w/w) on a dry basis |
|---|---|
| Aluminium silicate (KAOLIN) | 70.00-95.00 |
| Red iron oxide | 0.10-10.00 |
| Lycopene E160d | 0.10-15.0 |
| Methacrylic acid copolymer (EUDRAGIT ® S 100) | 1.00-10.00 |
| Potassium dihydrogen phosphate | 0.01-1.00 |
| Sodium phosphate dibasic | 0.10-1.00 |

*Corresponds to any of the synthetic viral combinations described herein.

TABLE 3

Wettable powder composition No. SfNPV003-1

| COMPONENT | (% w/w) on a dry basis |
|---|---|
| Viral suspension with a concentration between $10^4$ and $10^{11}$ occlusion bodies/mL* | 1.35 |
| Aluminium silicate (KAOLIN) | 77.95 |
| Red iron oxide | 1.36 |
| Lycopene E160d | 13.61 |
| Methacrylic acid copolymer (EUDRAGIT ® S 100) | 5.48 |
| Potassium dihydrogen phosphate | 0.04 |
| Sodium phosphate dibasic | 0.21 |

*Corresponds to any of the synthetic viral combinations described herein.

TABLE 4

Wettable powder composition No. SfNPV003-2

| COMPONENT | (% w/w) on a dry basis |
|---|---|
| Viral suspension with a concentration between $10^4$ and $10^{11}$ occlusion bodies/mL* | 2.50 |
| Aluminium silicate (KAOLIN) | 77.80 |
| Red iron oxide | 1.36 |
| Lycopene E160d | 13.61 |
| Methacrylic acid copolymer (EUDRAGIT ® S 100) | 4.48 |
| Potassium dihydrogen phosphate | 0.04 |
| Sodium phosphate dibasic | 0.21 |

*Corresponds to any of the synthetic viral combinations described herein.

TABLE 5

Wettable powder composition No. SfNPV003-3

| COMPONENT | (% w/w) on a dry basis |
|---|---|
| Viral suspension with a concentration between $10^4$ and $10^{11}$ occlusion bodies/mL* | 2.50 |
| Aluminium silicate (KAOLIN) | 77.80 |
| Red iron oxide | 2.36 |
| Lycopene E160d | 13.61 |
| Methacrylic acid copolymer (EUDRAGIT ® S 100) | 3.48 |
| Potassium dihydrogen phosphate | 0.04 |
| Sodium phosphate dibasic | 0.21 |

*Corresponds to any of the synthetic viral combinations described herein.

TABLE 6

Emulsifiable liquid concentrate composition - base

| COMPONENT | (% w/w) on a dry basis |
|---|---|
| Viral suspension with a concentration between $10^4$ and $10^{11}$ occlusion bodies/mL* | 0.66-6.60 |
| Methacrylic acid copolymer (EUDRAGIT ® S 100) | 0.00-5.00 |
| Aluminium silicate (KAOLIN) | 2.0-30.00 |
| Lycopene E160d | 0.05-5.00 |
| Boric acid | 0.05-5.00 |
| Vegetable oil | 10.00-70.00 |
| Oleic acid | 3.00-10.00 |
| Polisorbate 80 (TWEEN 80) | 1.00-10.00 |
| Sorbitan monostearate (SPAN 60) | 1.00-10.00 |

*Corresponds to any of the synthetic viral combinations described herein.

TABLE 7

Emulsifiable concentrate composition No. SfNPV003-4

| COMPONENT | (% w/w) on a dry basis |
|---|---|
| Viral suspension with a concentration between $10^8$ and $10^{11}$ occlusion bodies/mL | 3.40 |
| Methacrylic acid copolymer (EUDRAGIT ® S 100) | 0.15 |
| Aluminium silicate (KAOLIN) | 10.60 |
| Lycopene E160d | 2.84 |
| Boric acid | 0.50 |
| Vegetable oil | 66.49 |
| Oleic acid | 8.01 |
| Polisorbate 80 (TWEEN 80) | 4.24 |
| Sorbitan monostearate (SPAN 60) | 3.77 |

*Corresponds to any of the synthetic viral combinations described herein.

The biopesticidal compositions of the invention are effective for use in the biological control of insects from orders Hymenoptera, Diptera and Lepidoptera, preferably against *Spodoptera frugiperda* in all of its host crops, especially corn, rice, cotton, sugarcane and grasses. Furthermore, obtaining the compositions of the present invention does not require advanced technology and these are viable for application in agricultural industry.

The following Examples describe the present invention in greater detail. However, the inventive concept is not limited to these examples.

EXAMPLES

Example 1. Obtaining the Genotypes

A *S. frugiperda* nucleopolyhedrovirus (NPV003) and a *S. frugiperda* granulovirus (VG008) were isolated from larvae collected from a pasture in the Department of Córdoba (Colombia) (Gómez et al., 2010). Purified polyhedra containing various genotypes were naturally obtained from the nucleopolyhedrovirus NPV003.

The process for obtaining pure genotypes is described in FIG. 2, which shows how the purified viral suspension of NPV0003 were used to infect *S. frugiperda* larvae by oral administration, and hemolymph was extracted from the larvae at the point in the cycle during which budded virions were present (with a single nucleocapsid and a single genome).

By means of several dilutions, insect cells of the Sf9 line (*S. frugiperda* cell line) were infected. Then, individual cells containing a single genotype were selected and multiplied by means of injection into larvae, from which each individual genotype variant was purified after the death of the larvae. From these individual genotypes, combinations of the genotypes that were previously selected for their insecticidal activity were produced. Initially, the virions derived from treatment of occlusion bodies with alkaline solutions were released and injected into larvae. The co-occlusion of the selected genotypes occurred during the infection process. Meanwhile, combinations of the genotypes were obtained by combining the occlusion bodies that contain individually selected variants.

Example 2. Insecticidal Activity of the Viral Combinations

Insecticidal activity was evaluated by means of a bioassay in accordance with the droplet method described by Hughes and Wood (1981) and using the previously determined Lethal Concentration 50 ($CL_{50}$) of the wild-type virus NPV003, equal to $1 \times 10^5$ CI/mL. The treatments correspond to the wild-type virus NPV003, synthetic combination No. 1, synthetic combination No. 2 and an absolute control. The assay employed three repetitions per treatment, each with 15 neonate larvae, in a completely randomized design, and mortality was evaluated 7 days after inoculation. The results were analyzed by means of an ANOVA and a least significant difference (LSD) test (95%).

As a result of the assay, the absolute control exhibited a mortality rate of 6.66%, while the evaluated treatments exhibited significantly greater mortality rates (p<0.05). The employed concentration of wild-type virus NPV003 resulted in the expected mortality rate, 53.33%, while the assayed combinations (synthetic combinations 1 and 2) exhibited a significant increase (p=0.0168) in insecticidal activity, with mortality values of 80% and 70% for combinations 1 and 2, respectively.

The results are shown in Table 8, which confirm the enhancing effect of the synthetic combinations with the potential to be used as active ingredients in bioinsecticidal compositions.

TABLE 8

Mortality rate of neonate *S. frugiperda* larvae treated with wild-type virus NPV003 and two synthetic combinations at $1 \times 10^5$ CI/mL

| Repetition | NPV003 | Combination | Combination | Control |
|---|---|---|---|---|
| 1 | 53.00 | 67.00 | 73.00 | 6.66 |
| 2 | 46.00 | 87.00 | 73.00 | 6.66 |
| 3 | 60.00 | 87.00 | 66.00 | 6.66 |
| Average | 53.00 | 80.33 | 70.66 | 6.66 |

Example 3. Stability of the Compositions in Storage Conditions

For a composition formulated in accordance with Table 4 (No. SfNPV003-1 based on viral combination No. 1), 0.5 g samples were packed into vacuum-sealed metalized pouches having a 2 cm width and a 4 cm length. Formulated (formula No. SfNPV003-1 (NPV003-f)) and unformulated (NPV003-nf) wild-type isolate NPV003 were used as control treatments.

Nine samples of each treatment were stored in an incubator at 28±2° C. Insecticidal activity was evaluated by means of a bioassay before storage and after 1, 2 and 3 months of storage, in accordance with the droplet method described by Hughes and Wood (1981) and using the previously determined $CL_{90}$ of each viral inoculum.

To quantify the contaminant content, 9 mL of 0.1% Polisorbate 80 (TWEEN® 80) were added to one of the samples and decimal dilutions down to $1 \times 10^{-5}$ were performed. 100 µL from the last three dilutions were spread onto Petri dishes:

i) for the assessment of molds in potato dextrose agar medium supplemented with 0.1% octyl phenol ethoxylate (TRITON) (PD agar +TRITON);
ii) for the quantification of yeasts in yeast extract malt agar medium (YM agar), and;
iii) for bacterial counting in nutrient agar medium.

Each dilution was spread in triplicate. The result was expressed as the number of colony-forming unites per gram of product (CFU/g). The experimental design was completely randomized, with repeated measurements over time and all measurements performed in triplicate.

FIG. 5 shows that the wild-type virus NPV003 exhibited a 33% loss of its insecticidal activity when it was stored as an unformulated viral suspension for three months at 28° C. On the other hand, the wild-type virus NPV003 and the viral combination (combination 1) formulated as a wettable powder only exhibited an 11% loss of insecticidal activity when they were subjected to the same conditions as the unformulated virus NPV003, which proves the stabilizing effect offered by the formulation during the storage period.

Under the conditions of the study, the formulation reduced viral inactivation by 66% after three months of storage at a temperature of 28° C., an effect that could be increased at lower temperatures or in refrigeration conditions.

The loss kinetics of efficacy versus storage time of the formulated combination was fit to a curve of first-order kinetics with a 0.98 correlation coefficient. The shelf life of the product was estimated using the equation produced by this mathematical model, using 70% as the minimum acceptable efficacy rate. Based on this information, the product would be stable for 8 months of storage at 28° C., that is to say, without the need for a cold chain during transport, which reduces distribution costs and provides a time window large enough for the sale of the bioadditive.

As for the contaminant content, shown in FIG. 6, the microorganism content in the treatment corresponding to the unformulated suspension of wild-type virus NPV003 increases in direct proportion to the storage time, in increments greater than one logarithmic unit. On the other hand, the two tested formulated treatment (wild-type virus NPV003 and the viral combination, in wettable powder form), exhibited a significant reduction in contaminants, which was inversely proportional to the storage time.

This behavior is possibly due to the effect of the formulation process, which involves the removal of water from the product until the final humidity level in the product is less than 5%. The drying process causes the death of microorganisms, thereby reducing the contaminant load by two logarithmic units and then, the low humidity inhibits microbial metabolism and prevents the proliferation of contaminants, such as bacteria and fungi that are still viable in the formulation.

The reduction of contaminants in the formulation may be associated with the greater stability of its insecticidal activity, bearing in mind that microorganisms can negatively affect the integrity of viral particles during storage.

Example 4. Photostability Assay Under UVB Radiation

The treatments evaluated in this assay were unformulated wild-type virus NPV003 (aqueous suspension), wild-type virus NPV003 formulated as a wettable powder in accordance with formula No. SfNPV003-1 from Table 4, and the formulated viral combination (combination No. 1), also formulated as per SfNPV003-1. Suspensions were prepared at a concentration of $2 \times 10^7$ CI/mL.

200 µL of each suspension were placed in 5 wells of a row of a flat-bottomed 96-well microplate. The microplate was irradiated with a monochromatic light (wavelength=302 nm) for 2, 4 and 6 hours, at a distance of 10 cm from the light source. Before beginning the exposure to light, the first column of wells of the microplate was covered with aluminum foil (one well of each concentration), which corresponded to the treatment of no exposure of the virus to radiation (time=0 hours).

Every 2 hours, until 6 hours had elapsed, the next column of wells was covered, so that each column of the microplate represented a different duration of exposure to ultraviolet-B radiation. Subsequently, 200 µL of a 4% sucrose solution, which contained 1% blue food coloring agent, were added to each well, and a bioassay was performed to determine their insecticidal activity, in accordance with the droplet method described by Hughes and Wood (1981).

The formula from Schneider-Orelli (Zar 1999) was used to determine their efficacy, and these efficacy values were then used to calculate the remaining percentage of original activity using the following equation (Shapiro, 1989):

$$\% \text{ Original Activity} = (B/A) \times 100$$

where:
A: Efficacy of the unexposed virus
B: Efficacy of the virus exposed to UV radiation The normality of the data was estimated by means of a Shapiro-Wilk test (95%) and the homogeneity of variance was estimated using Bartlett's test (95%). Subsequently, the differences between treatments were proven by means of an LSD test (95%).

FIG. 7 shows the results of the assay, which demonstrates that the unformulated virus NPV003 exhibited a progressive and significant loss in activity as the irradiation time elapsed, exhibiting 49% inactivation after 6 hours of exposure to UVB light.

The wild-type virus NPV003 formulated as a wettable powder in accordance with formula No. SfNPV003-1 exhibited 11.6% inactivation, while the viral combination also formulated in accordance with formula No. SfNPV003-1 exhibited 5.8% inactivation, which confirms the photoprotectant effect of the formulation, which would prolong the preservation of the viral particles in the environment.

It should be noted that efficacy after 6 hours of irradiation was significantly greater for the formulated product based on the viral combination than the formulated product based on the wild-type virus NPV003, which also suggests that the viral combination possibly contributes to the greater photostability of the formulated product.

REFERENCES

1. Boucias, D. G., Pendland, J. C. 1998. Baculoviruses, in: Kluwer (Ed.), Principles of insect pathology. Academic Publishers, Norwell, pp. 111-146.
2. Braunagel, S. C., Summers, M. D. 1994. *Autographa californica* nuclear polyhedrosis virus, PDV, and ECV viral envelopes and nucleocapsids: structural proteins, antigens, lipid and fatty acid profiles. Virology 202: 315-328.
3. Duffy, S. P., Young, A. M., Morin, B., Lucarotti, C. J., Koop, B. F., & Levin, D. B. 2006. Sequence analysis and organization of the *Neodiprion abietis* nucleopolyhedrovirus genome. Journal of Virology 80: 6952-63.
4. Funk, C. J., Braunagel, S. C., Rohrmann, G. F. 1997. Regulation of Baculovirus Late and Very Late Gene Expression. New York: Plenum
5. Gómez, J., Guevara, J., Cuartas, P., Espinel, C., Villamizar, L. 2013. Microencapsulated *Spodoptera frugiperda* nucleopolyhedrovirus: insecticidal activity and effect on arthropod populations in maize. Biocontrol Science and Technology 23: 829-846.
6. Gómez, J.; Guevara, J.; Barrera, G.; Cotes, A.; Villamizar, L. 2010. Aislamiento, identificación y caracterización de nucleopoliedrovirus nativos de *Spodoptera frugiperda* en Colombia. [Isolation, identification and characterization of *Spodoptera frugiperda* wild-type nucleopolyhedrovirus in Colombia.] Revista Facultad Agronomia. Medellín 63: 5511-5520.
7. Herniou, E. A., Olszewski, J. A., Cory, J. S., O'Reilly, D. R. 2003. The genome sequence and evolution of baculoviruses. Annual Review of Entomology 48: 211-234.
8. Herniou, E. A, Olszewski, J. A., O'Reilly, D. R., Cory, J. S. 2004. Ancient coevolution of baculoviruses and their insect hosts. Journal of Virology 78: 3244-3251.
9. Hughes, P. R., Wood, H. A. 1981. A synchronous peroral technique for the bioassay of insect viruses. Journal of Invertebrate Pathology 37: 154-159.
10. ICTV, 2012. International Committee on Taxonomy of viruses.
11. Inceoglu, A. B., Kamita, S. G., Hammock, B. D. 2006. Genetically modified baculoviruses: a historical overview and future outlook. Advances in virus research 68: 323-360.
12. Jehle, J. A., Lange, M., Wang, H. L., Hu, Z. H., Wang, Y. J., Hauschild, W. 2006. Molecular identification and phylogenetic analysis of baculoviruses from Lepidoptera. Virology 346: 180-193.
13. Jenkins, N. & Grzywacz, D. 2003. Towards the standardization of quality control of fungal and viral biocontrol agents. In Qual Control Prod Biol Control agents theory Test Proced, pp. 247-263. Edited by J. C. van Lenteren. Wallinford, UK: CAB International.
14. Lahlalia R, Serrhinib M, Jijakl M. 2006. Studying and modelling the combined effect of temperature and water activity on the growth rate of *P. expansum*. International Journal of Food Microbiology. 103:315-322.
15. Lasa, R., Pagola, I., Ibanez, I., Belda, J. E., Williams, T., Caballero, P. 2007. Efficacy of *Spodoptera exigua* multiple nucleopolyhedrovirus as a biological insecticide for beet armyworm control in greenhouses of southern Spain. Biocontrol Science and Technology 17: 221-232.
16. Miele, S. A. B., Garavaglia, M. J., Belaich, M. N., 2011. Baculovirus: molecular insights on their diversity and conservation. Int. Journal of Evolutionary Biology 211: 37-42.
17. Muñoz, D., Castillejo, J. I., Caballero, P. 1998. Naturally occurring deletion mutants are parasitic genotypes in a wild-type nucleopolyhedrovirus population of *Spodoptera exigua*. Applied and Environmental Microbiology 64: 4372-4377.
18. Muñoz, D., Murillo, R., Krell, P. J., Vlak, J. M., Caballero, P. 1999. Four genotypic variants of a *Spodoptera exigua* nucleopolyhedrovirus (Se-SP2) are distinguishable by a hypervariable genomic region. Virus Research 59: 61-74.
19. Murillo, R., Muñoz, D., Williams T., Caballero, P. 2006. Genetic and phenotypic variability in *Spodoptera exigua*

20. Ravensberg, W. 2011. A roadmap to the successful development and commercialization of microbial pest control products for control arthropods. Vol. 10.
21. Santos A., García M., Cotes A. M., Villamizar L. 2012. Efecto de la formulación sobre la vida util de bioplaguicidas a base de dos aislamientos colombianos de *Trichoderma koningiopsis* Th003 y *Trichoderma asperellum* Th034. [Effect of the formulation on the shelf life of biopesticides based on two Colombian isolates from *Trichoderma* koningiopsis Th003 and *Trichoderma asperellum* Th034.] Revista Iberoamericana de Micología 29:150-156.
22. Schneider-Orelli, O., 1947. Entomologisches Praktikum-Einfürung in die land—un forstwirtschafliche Insektenkunde. Sauerländer & Co, Aarau, Germany.
23. Shapiro, M. 1989. Congo red as an ultraviolet protectant for the gypsy moth (Lepidoptera:Lymantriidae) nuclear polyhedrosis virus. Journal of Economical Entomology. 82: 548-550.
24. Simón, O., Williams, T., López-Ferber, M., Caballero, P., 2004. Genetic structure of a *Spodoptera frugiperda* nucleopolyhedrovirus population: High prevalence of deletion genotypes. Applied and Environmental Microbiology 70: 5579-5588.
25. Simón, O., Williams, T., López-Ferber, M., Caballero, P., 2005. Functional importance of deletion mutant genotypes in an insect nucleopolyhedrovirus population. Applied and Environmental Microbiology 71, 4254-4262.
26. Slack, J., Arif, B. M., 2007. The baculoviruses occlusion-derived virus: Virion structure and function. Advances in virus research 69: 99-165.
27. Theilmann, D. A., Blissard, G. W., Bonning, B., Jehle, J., O'Reilly, D. R., Rohrmann, G. F., Theim, S., Vlak, J., 2005. Family baculoviridae. In: Fauquet, C. M., Mayo, M. A., Maniloff, J., Desselberger, U., Ball, L. A. (Eds.), Virus Taxonomy, Eighth Report of the International Committee on Virus Taxonomy. Elsevier Press, San Diego, pp. 177-185.
28. Villamizar, L., Barrera, G., Cotes, A. M. & Martinez, F. 2010. Eudragit S100 microparticles containing *Spodoptera frugiperda* nucleopolyhedrovirus: physicochemical characterization, photostability and in vitro virus release31. Journal of Microencapsulation 27: 314-24
29. Villamizar, L., Zeddam, J., Espinel, C., Cotes, A. M. 2005. Implementación de técnicas de control de calidad para la producción de un bioplaguicida a base del granulovirus de *Phthorimaea operculella* PhopGV. [Implementation of quality control techniques for the production of a biopesticide based on *Phthorimaea operculella* granulovirus PhopGV.] Revista Colombiana de Entomología 31: 127-132.
30. Wang, Y.; Jehle, J. A. 2009. Nudiviruses and other large, stranded circular DNA viruses of invertebrates: New insights on an old topic. Journal of Invertebrate Pathology 101: 187-193. Zar, J. 1999
31. Biostatistical Analysis. 4th Edition Prentice Hall. New Jersey.

The invention claimed is:

1. A biopesticidal composition comprising:
   a) occlusion bodies of the nucleopolyhedrovirus NPV003, isolated from *Spodoptera frugiperda* further comprising the sequences sf23 and sf24, as set forth in SEQ ID NOs.: 1 and 2 respectively;
   b) biological enhancer which is granulovirus VG008, characterized by a PstI restriction pattern and further characterized because its genome comprises a specific sequence SFGV24 as set forth in SEQ ID NO. 5, or proteins derived thereof; and
   c) excipients selected from the group consisting of ultraviolet protectant coadjuvants, diluents, coating polymers, surfactants and/or pH regulators or combinations thereof.

2. The biopesticidal composition of claim 1, in solid form such as powder, a granule, a tablet or a pellet, or in liquid form such as a suspension, an emulsifiable concentrate or an emulsion, optionally mixed with compost, fertilizers, bio-additives, vegetable extracts or agrochemicals.

3. The biopesticidal composition of claim 1 further comprising:
   a) a concentration between $10^4$ and $10^{11}$ occlusion bodies/mL;
   b) wherein the excipients are selected from diluents or carriers, pigments, coloring agents, coating polymer, potassium dihydrogen phosphate and sodium phosphate dibasic and water.

4. The biopesticidal composition of claim 1 comprising:

| COMPONENT | (% w/w) on a dry basis |
|---|---|
| a concentration between $10^4$ and $10^{11}$ occlusion bodies/mL | 0.50-8.50 |
| Aluminium silicate | 70.00-95.00 |
| Red iron oxide | 0.10-10.00 |
| Lycopene-E160d | 0.10-15.00 |
| Methacrylic acid copolymer | 1.00-10.00 |
| Potassium dihydrogen phosphate | 0.01-1.00 |
| Sodium phosphate dibasic | 0.10-1.00. |

5. The biopesticidal composition of claim 1 comprising:

| COMPONENT | (% w/w) on a dry basis |
|---|---|
| a concentration between $10^4$ and $10^{11}$ occlusion bodies/mL | 1.35 |
| Aluminium silicate | 77.95 |
| Red iron oxide | 1.36 |
| Lycopene E160d | 13.61 |
| Methacrylic acid copolymer | 5.48 |
| Potassium dihydrogen phosphate | 0.04 |
| Sodium phosphate dibasic | 0.21. |

6. The biopesticidal composition of claim 1 comprising:

| COMPONENT | (% w/w) on a dry basis |
|---|---|
| a concentration between $10^4$ and $10^{11}$ occlusion bodies/mL | 2.5 |
| Aluminium silicate | 77.8 |
| Red iron oxide | 1.36 |
| Lycopene E160d | 13.61 |
| Methacrylic acid copolymer | 4.48 |
| Potassium dihydrogen phosphate | 0.04 |
| Sodium phosphate dibasic | 0.21. |

7. The biopesticidal composition of claim 1, comprising:

| COMPONENT | (% w/w) on a dry basis |
|---|---|
| a concentration between $10^4$ and $10^{11}$ occlusion bodies/mL | 2.5 |
| Aluminium silicate | 77.8 |
| Red iron oxide | 2.36 |
| Lycopene E160d | 13.61 |
| Methacrylic acid copolymer | 3.48 |
| Potassium dihydrogen phosphate | 0.04 |
| Sodium phosphate dibasic | 0.21. |

8. The biopesticidal composition of claim 1, comprising:

| COMPONENT | (% w/w) on a dry basis |
|---|---|
| a concentration between $10^4$ and $10^{11}$ occlusion bodies/mL | 0.66-6.60 |
| Methacrylic acid copolymer | 0.00-5.00 |
| Aluminium silicate | 2.0-30.00 |
| Lycopene E160d | 0.05-5.00 |
| Boric acid | 0.05-5.00 |
| Vegetable oil | 10.00-70.00 |
| Oleic acid | 3.00-10.00 |
| Polysorbate 80 | 1.00-10.00 |
| Sorbitan Monostearate | 1.0-10.00 | wherein the composition is an emulsifiable concentrate.

9. The biopesticidal composition of claim 1 comprising:

| COMPONENT | (% w/w) on a dry basis |
|---|---|
| a concentration between $10^8$ and $10^{11}$ occlusion bodies/mL | 3.4 |
| Methacrylic acid copolymer | 0.15 |
| Aluminium silicate | 10.6 |
| Lycopene E160d | 2.84 |
| Boric acid | 0.5 |
| Vegetable oil | 66.49 |
| Oleic acid | 8.01 |
| Polysorbate 80 | 4.24 |
| Sorbitan Monostearate | 3.77 | wherein the composition is an emulsifiable concentrate.

* * * * *

SEQUENCE LISTING

<160> NUMBER OF SEQ ID NOS: 9

<210> SEQ ID NO 1
<211> LENGTH: 214
<212> TYPE: DNA
<213> ORGANISM: Nucleopolyhedrovirus

<400> SEQUENCE: 1

```
gcttgtgcgt tgtcgttgat cgtacagaga taataactaa aatacacccc atcactaaga      60
aaaaaattaa aattgacgta tctaataaat acattaatag gatgaagaag acgctgataa     120
agtggggcta tcctgtgaaa tttgcaaaat ttgacgagtt taaaggatac aagtacgaca     180
ttgacacgga cgactgggac cgagtcgact acaa                                 214
```

<210> SEQ ID NO 2
<211> LENGTH: 166
<212> TYPE: DNA
<213> ORGANISM: Nucleopolyhedrovirus

<400> SEQUENCE: 2

```
tcgtcggcat catactgctc tcggtggaca agtttgtgtc catacccatc atacagctgt      60
accagatcgc gtaccagcaa ctgcagatat cgccgtttta cgtgacgctg acgctcatgc     120
tgctcaccac cgttggtgga ctgtcgacga aaaccatgcg aacgtg                    166
```

<210> SEQ ID NO 3
<211> LENGTH: 19
<212> TYPE: DNA
<213> ORGANISM: Nucleopolyhedrovirus

<400> SEQUENCE: 3

```
ccgataaggt tatatctga                                                   19
```

```
<210> SEQ ID NO 4
<211> LENGTH: 19
<212> TYPE: DNA
<213> ORGANISM: Nucleopolyhedrovirus

<400> SEQUENCE: 4
tcaataactt cttcgtgca                                                    19

<210> SEQ ID NO 5
<211> LENGTH: 203
<212> TYPE: DNA
<213> ORGANISM: Nucleopolyhedrovirus

<400> SEQUENCE: 5
agatatcacc tttgaagaca ttgattcgat ctacgacgca gaaacgcaac tcgacaaagc        60
ttacgataac gttaaatggg aggacaaata caaggaattg ctagaccaat acaataaaga       120
taaagaaaaa tgggagaaaa aatacacaga gcttatgaat caaaatacag tcgacgagga       180
caaatggaca acagaaaaga aga                                               203

<210> SEQ ID NO 6
<211> LENGTH: 20
<212> TYPE: DNA
<213> ORGANISM: Nucleopolyhedrovirus

<400> SEQUENCE: 6
gcttgtgcgt tgtcgttgat                                                   20

<210> SEQ ID NO 7
<211> LENGTH: 20
<212> TYPE: DNA
<213> ORGANISM: Nucleopolyhedrovirus

<400> SEQUENCE: 7
ttgtagtcga ctcggtccca                                                   20

<210> SEQ ID NO 8
<211> LENGTH: 20
<212> TYPE: DNA
<213> ORGANISM: Nucleopolyhedrovirus

<400> SEQUENCE: 8
tcgtcggcat catactgctc                                                   20

<210> SEQ ID NO 9
<211> LENGTH: 20
<212> TYPE: DNA
<213> ORGANISM: Nucleopolyhedrovirus

<400> SEQUENCE: 9
cacgttcgca tggttttcgt                                                   20
```